(12) United States Patent
Aufderheide et al.

(10) Patent No.: US 7,656,515 B2
(45) Date of Patent: Feb. 2, 2010

(54) APPARATUS AND METHOD FOR ANALYSIS OF OPTICAL STORAGE MEDIA

(75) Inventors: Jeffrey Alan Aufderheide, Salida, CA (US); James Henry Eckerman, Boulder Creek, CA (US); Ian Blair Freeman, Fremont, CA (US); John Clarence Meyer, Firestone, CO (US); Charles Calvin Brooks Partee, Lyons, CO (US); Timothy Joseph Skwiot, Winona, MN (US)

(73) Assignee: CheckFlix, Inc., Lyons, CO (US)

( * ) Notice: Subject to any disclaimer, the term of this patent is extended or adjusted under 35 U.S.C. 154(b) by 294 days.

(21) Appl. No.: 11/558,759

(22) Filed: Nov. 10, 2006

(65) Prior Publication Data

US 2007/0104061 A1    May 10, 2007

Related U.S. Application Data

(60) Provisional application No. 60/735,331, filed on Nov. 10, 2005.

(51) Int. Cl.
*G01N 21/00* (2006.01)

(52) U.S. Cl. ............................ 356/237.1; 356/237.2
(58) Field of Classification Search .... 356/237.1–237.5
See application file for complete search history.

(56) References Cited

U.S. PATENT DOCUMENTS

| | | | |
|---|---|---|---|
| 4,954,723 A | 9/1990 | Takahashi et al. | |
| 5,248,973 A | 9/1993 | Babu et al. | |
| 6,262,432 B1 | 7/2001 | Brunfeld et al. | |
| 6,721,248 B2 | 4/2004 | Kubo et al. | |
| 7,016,031 B2 | 3/2006 | Meeks | |
| 7,061,601 B2 | 6/2006 | Meeks | |
| 7,289,405 B2 | 10/2007 | Kim et al. | |
| 7,403,279 B2 * | 7/2008 | Tohyama et al. | 356/237.2 |

FOREIGN PATENT DOCUMENTS

| | | |
|---|---|---|
| EP | 1522846 | 4/2005 |
| EP | 1679504 | 7/2006 |
| GB | 2299404 | 10/1996 |
| JP | 60166809 | 8/1985 |
| JP | 62163952 | 7/1987 |
| JP | 02163639 | 6/1990 |
| WO | WO2005040775 | 5/2008 |

OTHER PUBLICATIONS

International Search Report, PCT/US06/60802, 8 pages, Feb. 6, 2008.
European Search Report, EP06846278.7, 11 pages, Dec. 2, 2008.

\* cited by examiner

*Primary Examiner*—Michael P Stafira
(74) *Attorney, Agent, or Firm*—Dorsey & Whitney LLP

(57) ABSTRACT

Various apparatus and related methods are disclosed that are capable of detecting surface defects on an optical storage media. One example of an apparatus is configured to direct at least one light signal, which may be from one or more lasers, on an outer surface of an optical storage medium, such as a CD, DVD or the like, which includes encoded data. The light encounters both the optical storage media surface as well as any smudges, scratches, dents, or other defects thereon. Some or all of the light reflected from the defects and the surface are detected by one or more detectors, which may be a photo-diode. The detector(s) produce an output signal commensurate with the detected reflected light, which output is processed to determine whether the encoded data may be accurately read from the optical storage media.

31 Claims, 11 Drawing Sheets

APPARATUS AND METHOD FOR ANALYSIS OF OPTICAL STORAGE MEDIA

CROSS-REFERENCE TO RELATED APPLICATIONS

This non-provisional application claims the benefit of U.S. Provisional Application No. 60/735,331, entitled "Apparatus and Method for Analysis of Optical Storage Media," filed Nov. 10, 2005, which is hereby incorporated by reference herein. This application is also related to U.S. provisional application No. 60/865,197 entitled "Method for Using Optical Storage Media Analysis," filed Nov. 10, 2006, which is also hereby incorporated by reference herein.

FIELD OF THE INVENTION

Aspects of the invention involve an apparatus and method for analyzing the surface of an optical storage medium. Aspects of the invention also involve an apparatus and method of determining if a given optical storage medium ("OSM"), of various possible types, can be processed in an optical storage device ("OSD"), of various possible types, that can read or write data to the OSM based on the detection of various possible defects that can prevent or inhibit processing. Various methods and apparatus conforming to aspects of the invention can be integrated into an existing OSD, can be integrated into a standalone device whose main purpose is to analyze OSM, and can be presented in other embodiments.

BACKGROUND

The information storage industry is driven by market demands to increase continually the capacity and performance of devices for storing information. One of the needs is distribution of information (spatial communication) to various locations and retention of information (temporal communication) to be accessed at a later time. One popular application for information storage is storage of video information, such as movies, TV shows, and home videos. Yet another popular application is storage of music information. Another application is the storage and distribution of software to end-users. Driven by and reflecting this market demand, a variety of storage formats have been introduced into the market to fill various needs.

There are numerous methods of storing information, such as through printed matter (e.g., books and magazines), semiconductor-based RAM and FLASH memories, magnetic-based MRAM or bubble memories, magnetic-based Winchester-type disc drives, optical storage using phase-change or prefabricated or "burned" media, and holographic storage, among others. There are certain advantages and disadvantages of each type and, over time, certain types of storage tend to dominate certain applications.

The compact disc ("CD"), a type of OSM, was introduced in the 1970s and soon became a popular method for storage and distribution of music information due to certain advantages it held over the then state-of-the-art (cassette tapes and LP records). The CD medium was also adopted for storage and distribution of computer software due to certain advantages it held over the then state-of-the-art (floppy discs). Further advances in media and CD recorder/player technology, types of readback devices, allowed companies and consumers to record their own CDs, using several different formats available, to store information of many types from music and video, to pictures and images, to software and data. The capacity of CDs varied but was on average around 600 MB per disc. This was sufficient for many applications, but was not adequate to store a motion picture without considerable compression.

The DVD (sometimes styled as Digital Video Disc or Digital Versatile Disc although the exact expansion (if any at all) of the acronym is not generally agreed on), another type of OSM, was introduced in the 1990s and quickly became popular for distribution of pre-recorded video information, such as movies and extra features. The DVD format also allows for storage and distribution of software and other forms of data. Further advances in DVD media and DVD recorder/player technology, another type of OSD, allowed companies and consumers to record their own DVDs to store information of many types from music and video, to pictures and images, to software and data. The capacity of DVDs vary, some DVDs have a capacity of about 4.7 Gbytes per DVD. This is sufficient to store a full length motion picture feature plus other information that is of interest and benefit to consumers. The adoption of DVD technology into the market was one of the most rapid market penetration stories of our time.

New technologies are now emerging to store even more data on an optical storage medium. For example, two new competing formats (others may emerge) are popularly referred to as Blu-Ray and HD-DVD. These formats can each store over 15 Gbytes per disc. This enables the storage and distribution of an HDTV-format movie on a single disc. Information storage using the principles of holography is also under development. Other improvements and formats will doubtless be introduced from time to time in this competitive market.

In general conceptual terms, the physical structure and operational principles of most optical storage methods is similar. FIG. 1 is a partial side section view of an OSM 10. For the purposes of illumination but not by way of limitation, binary data is encoded and recorded onto the disc by differences in the height of the recording layer (generally called "lands" 12 and "pits" 14). Data may also be recorded using changes in the phase of the material, or other methods. The OSM includes a substrate 16 of acrylic or other material. In a phase-change based OSM, a layer of the appropriate material is included in the substrate. In an OSM that uses difference in height, the pits and lands are encoded in the substrate. A protective coating 18, such as a polycarbonate, is applied over the substrate. The coating is optically transparent, at least for the wavelength of the laser used to read the data encoded from the pits and lands. An aluminized layer 20 may also be applied to the substrate over the pits 14 and lands 12. The aluminized layer improves reflection of the laser from the pits and lands. A label 22 may be on the substrate 18.

The laser is used to scan the disc and read back the data by detecting the variation in the reflected light. The data is stored in microscopic grooves or "tracks" running in a spiral around the disc. The OSD uses laser beams to scan these grooves, where minuscule reflective bumps (the lands) and non-reflective holes (the pits) aligned along the grooves modulate the laser signal which, when properly decoded, represents the zeros and ones of digital information.

DVD technology writes in smaller "pits" to the recordable media than CD technology. Smaller pits mean that the drive's laser must produce a smaller spot. DVD technology achieves this by reducing the laser's wavelength from the 780 nanometer ("nm") infrared light used in standard CD drives to about 625 nm-650 nm red light.

Smaller data pits allow more pits per data track. The minimum pit length of a single layer DVD-RAM is 0.4 micron as compared to 0.834 micron for a CD. Additionally, DVD tracks are closer together, allowing more tracks per disc.

Hence, track pitch—the distance from the center of one part of the spiral information or "track" to the adjacent part of the track—is smaller. On a 3.95 GB DVD-R, track pitch is 0.8 microns; CD track pitch is 1.6 microns. On 4.7 GB DVD-R media, an even smaller track pitch of 0.74 microns helps boost storage capacity.

These narrow tracks require special lasers for reading and writing—which can't read CD-ROMs, CD-Rs, CD-RWs, or audio CDs. DVD-ROM drive makers solved the problem by putting two lasers in their drives: one for DVDs, the other for CDs. To facilitate the focusing of the laser on smaller pits, DVD media uses a thinner plastic substrate than do CDs. Further, DVD media has a thinner protective coating that the laser must pass through to reach the pits to record or read data than does CD media. This reduction originally resulted in discs that were 0.6 mm thick—half the thickness of a CD. Even single-sided DVDs have two substrates, even though one isn't capable of holding data. Double-sided discs with two data surfaces must be turned over to read data on each side. In other OSMs, the information can be stored as phase changes in the media, dye changes, or in the direction of magnetization in a magneto-optical storage medium, among others.

In various OSM, then, the data layer is protected by a protective surface 18 that is substantially optically transparent. In CDs and DVDs, it is typically a polycarbonate material. One of the significant problems that current users of optical storage media face is damage to the OSM protective surface. This can scatter or change the behavior of the reflected or transmitted light to the point that the data can no longer be read or written or both. The OSM error correction coding ("ECC") can handle errors of a certain size, depending on the OSD, but errors larger than that threshold cause the OSD to be unable to read or write through the damage. In DVD players, this can be manifested as skipping, freezing, or an inability to even recognize the DVD's presence. In CD players, it can manifest itself as a high-pitched and annoying click, skipping, freezing, or an inability to even recognize the CD's presence. The frequency of this damage has been growing year over year as the rapid market penetration of OSM has reached relatively unsophisticated consumers (e.g. children) who do not treat the fragile protective surface with proper care.

Conventional methods exist to identify and alleviate problems reading or writing data to an OSM. Such conventional materials typically involve checking a data stream read from the OSM for errors, error correction code circuitry, and monitoring read retry requests. What is needed is a way to analyze the protective surface of an OSM. What is also needed is a way to determine whether data can be successfully read as well as written to an OSM. These and other needs are addressed by implementations and aspects of the present invention, as set forth in further detail below.

SUMMARY

One aspect of the invention involves a method for analyzing the surface of an optical storage medium. The method includes the operations of directing at least one light signal on an outer surface of an optical storage medium. The optical storage medium includes encoded data. The method further includes detecting some portion of the at least one light signal reflected from the outer surface of the optical storage medium. And, the method also involves determining whether the encoded data may be accurately read as a function of detecting some portion of the at least one light signal reflected from the outer surface.

Another aspect of the invention involves an apparatus for analyzing an optical storage medium. The apparatus, or "certifier," includes a platform configured to support the optical storage medium, which defines at least one side having a data layer. The apparatus further includes at least one light positioned to illuminate the at least one side having a data layer and at least one light detector positioned to receive light reflected from the optical storage medium and provide an output signal as function of the received reflected light. Finally, the apparatus includes at least one circuit element configured to receive the output signal from the light detector and to provide an output indicative of the integrity of the at least one side having a data layer.

These and many other aspects and implementations of the present invention are set forth in greater detail below.

BRIEF DESCRIPTION OF THE DRAWINGS

Before explaining the disclosed implementations in detail, it is to be understood that the invention is not limited in its application to the details of the particular arrangement shown, because the invention is capable of other embodiments. Moreover, aspects of the invention may be set forth in different combinations and arrangements to define inventions unique in their own right. Also, the terminology used herein is for the purpose of description and not of limitation. Thus, the present invention is not intended to be limited to the embodiments shown but is to be accorded the widest scope consistent with the principles and features described herein including alternatives, modifications and equivalents, as defined within the scope of the appended claims. It is noted that the drawings are not to scale and are diagrammatic in nature in a way that is thought to best illustrate features of interest.

DESCRIPTION OF EMBODIMENTS

Figure 1:
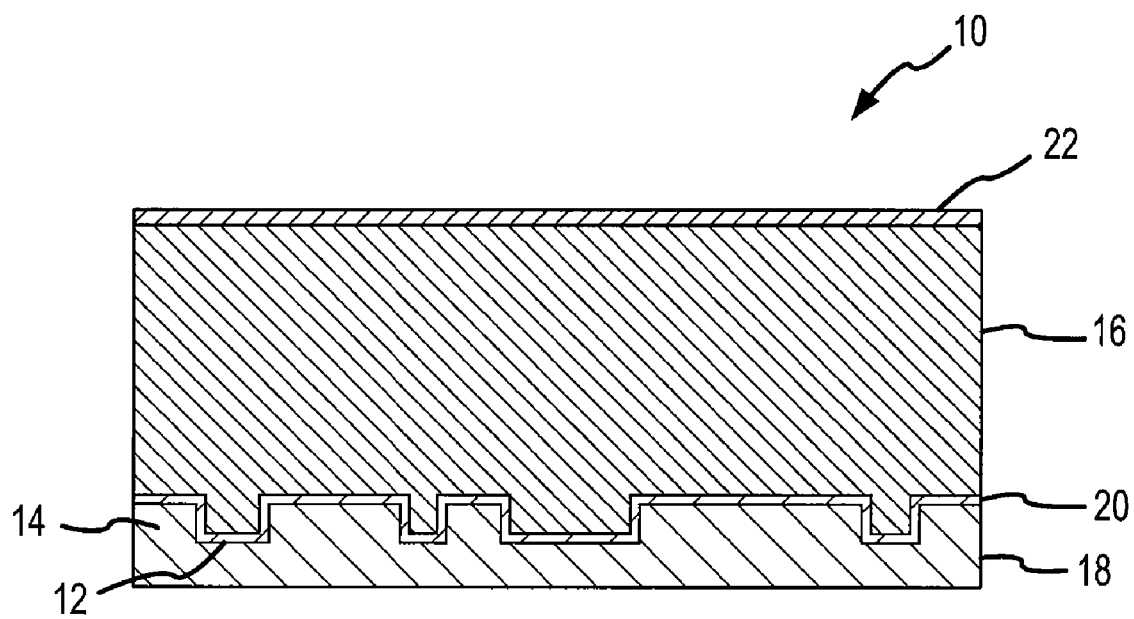
FIG. 1 is a representative section view of an exemplary optical storage medium.

Embodiments conforming to aspects of the invention may involve a method and device for analyzing and inspecting the surface of optical storage media ("OSM") to determine the topographical properties of the surface. Particularly, embodiments can detect the absence or presence of features on a given OSM, commonly referred to as defects, such as, but not limited to, scratches, dings, dust, dirt, fingerprints, other organic or inorganic material, bends or creases, cracks, or other foreign objects partially or fully embedded in or resident upon the surface. The presence of such surface defects can, in some instances, affect the ability of an optical storage device ("OSD") to read or write data from or to the OSM.

As such, embodiments conforming to aspects of the invention can be configured to determine if the presence, size, or prevalence of the defects are such that an OSD can or cannot read or write the data reliably. The analysis may also be conducted to determine if some, but not all, OSD can read or write the information. Moreover, the analysis may take into account a particular type of OSD or OSM and determine the likelihood of reliable data extraction or data addition from or to the particular OSD and/or OSM. Embodiments of the invention may further be configured to determine and identify the type of a defect so that a user can respond appropriately. OSM that can be characterized, analyzed, and/or inspected by embodiments described herein include by way of example, but are not limited to, DVD, DVD-ROM, DVD-R, DVD/R-W, DIVX, DVD-Audio, CD, CD-ROM, CD-WORM, CD-R/W, SACD, Blu-Ray, HD-DVD, game discs, holographic, and other types of optical storage media that may be developed in the future from time to time.

Unlike conventional, so-called "direct data" methods for measuring the read back quality of an OSM, embodiments described herein do not only rely on reading the data in order to compare it, checking the data stream for errors, using error correction code circuitry, or monitoring read retry requests from a player; rather, embodiments conforming to aspects of the invention can analyze the protective surface of an OSM to determine if the surface will prevent or inhibit the data from being read or written. These conventional methods, however, may be used to supplement the surface technique and implementation set forth herein. Conventional methods offer no known way of determining if the OSM can be successfully written, other than verifying the written data by reading it back.

Surface analysis techniques and configurations conforming to aspects of the invention are not optimal to detect defects in the data layer, which lies beneath the protective surface, but because these are rarer than defects in the exposed surface of the OSM, the compromise is acceptable. The data is stored in the reflective pits and non-reflective landings and covered with a protective coating. It is the exposed protective surface that gets scratched, smudged, dented, or otherwise damaged. These defects diffract the laser light from the OSD player and obscure the data layer beneath, thereby making it difficult to read or write the data layer. Nonetheless, as some portion of the light transmitted on an OSM will transmit through the outer layers, including the protective coating, and to the data layer, surface analysis implementations conforming to aspects of the invention may be configured to detect defects in the data layer, either alone or in conjunction with detecting defects in the outer layers.

Surface analysis may be employed alone or in combination with conventional direct data analysis techniques. In combination, surface analysis techniques and direct data analysis may determine data read capability despite extensive surface defects. Surface analysis technique and apparatus described herein can offer much increased speed over conventional direct data error detection methods that actually read the data. Embodiments may also analyze the surface characteristics of an OSM to determine the nature of the defect and recommend corrective action. Various embodiments can be used singly or jointly to good effect.

Figure 2:
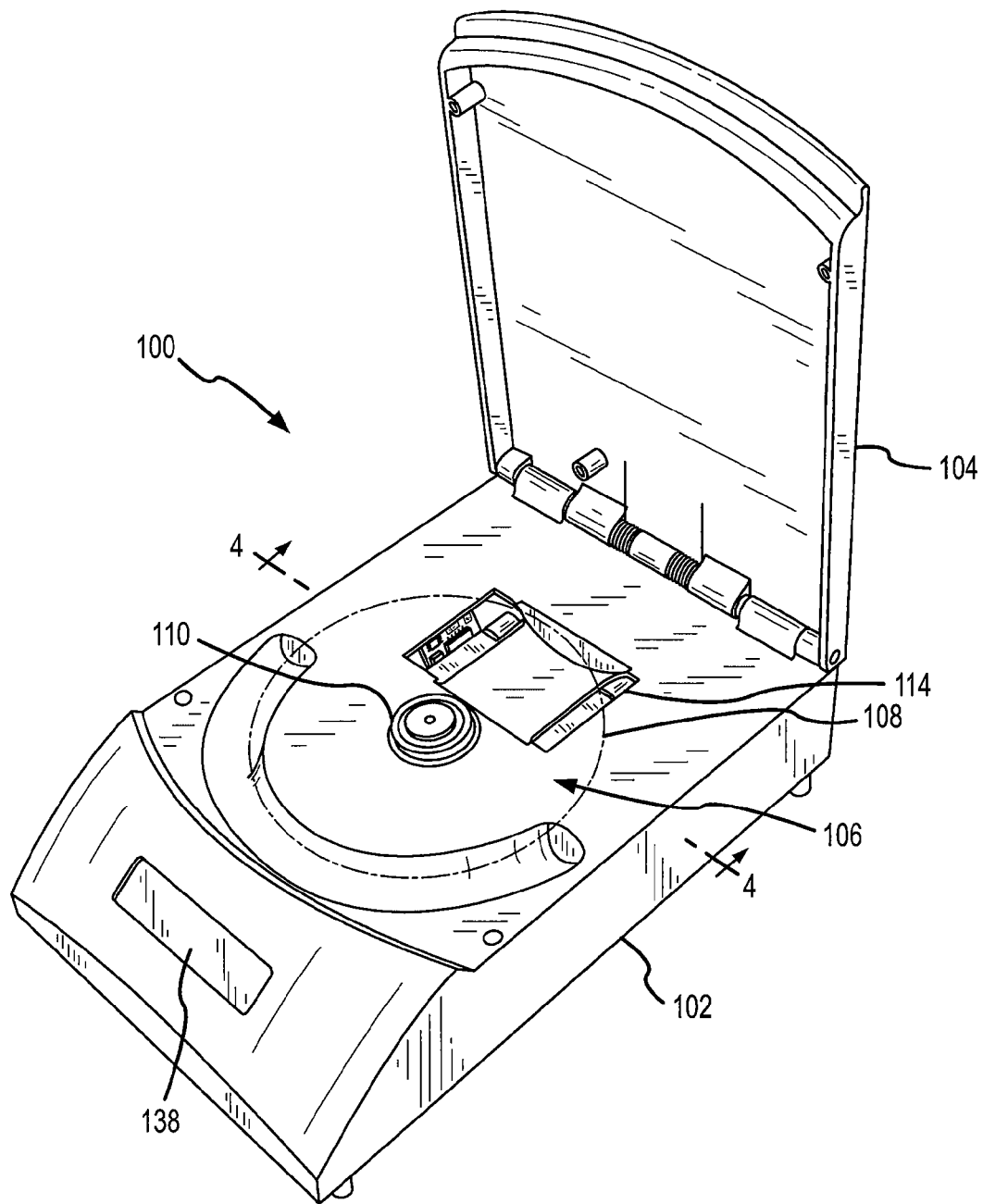
FIG. 2 is an isometric view of an optical storage media analyzer or "certifier," conforming to aspects of the present invention.
Figure 3A:
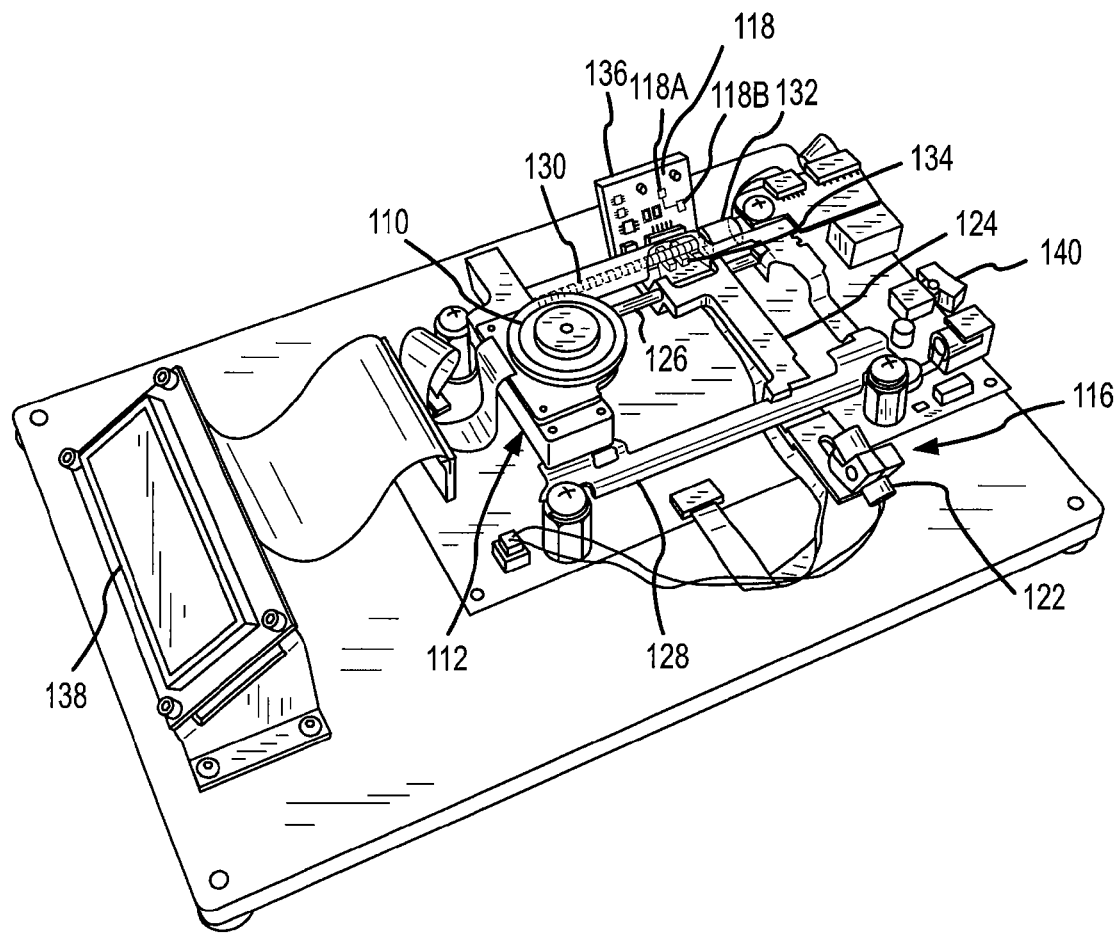
FIG. 3A is an isometric view of the optical storage media analyzer set forth in FIG. 2, with a cover removed to illustrate various electronics and to show a carrier, laser assembly and detector assembly in a first position, which may be a starting position of a scanning operation.
Figure 3B:
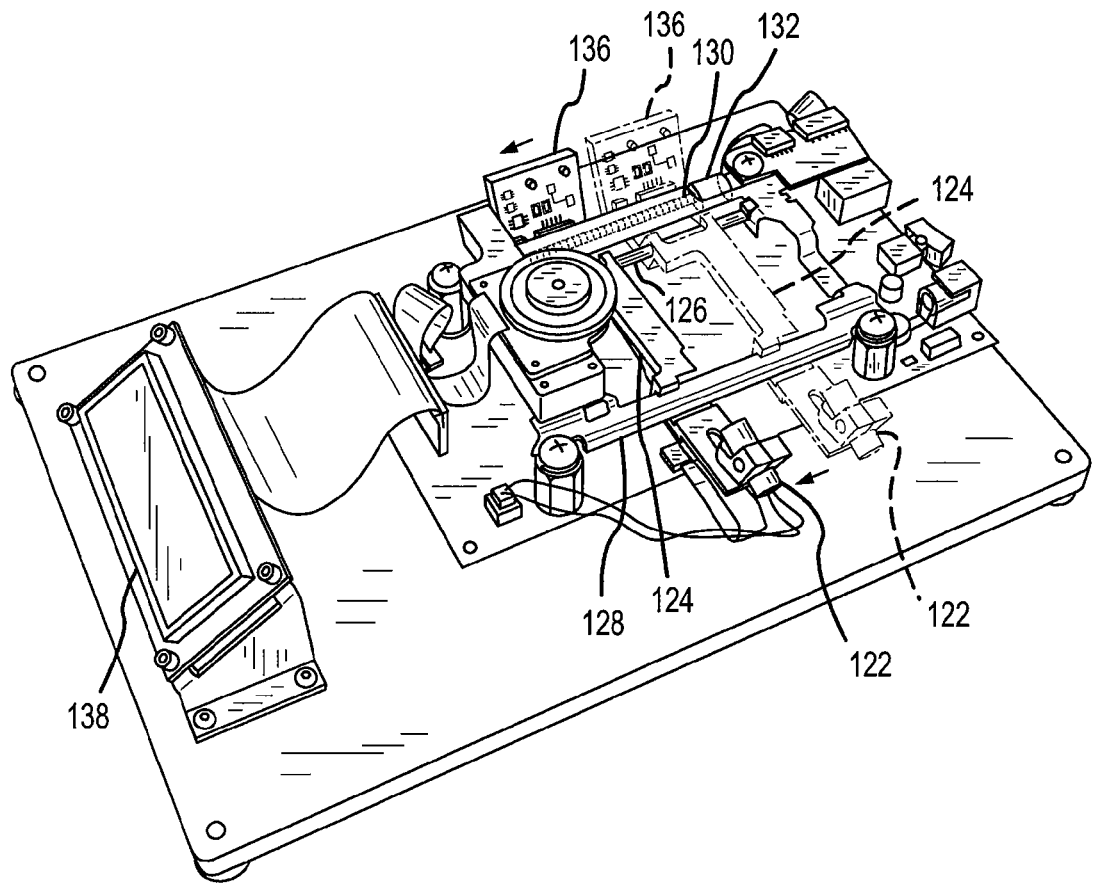
FIG. 3B is an isometric view of the optical storage media analyzer set forth in FIG. 3A, with the cover removed to illustrate various electronics and to show the carrier, laser assembly and detector assembly in a second position, which may be an ending position of a scanning operation.
Figure 4:
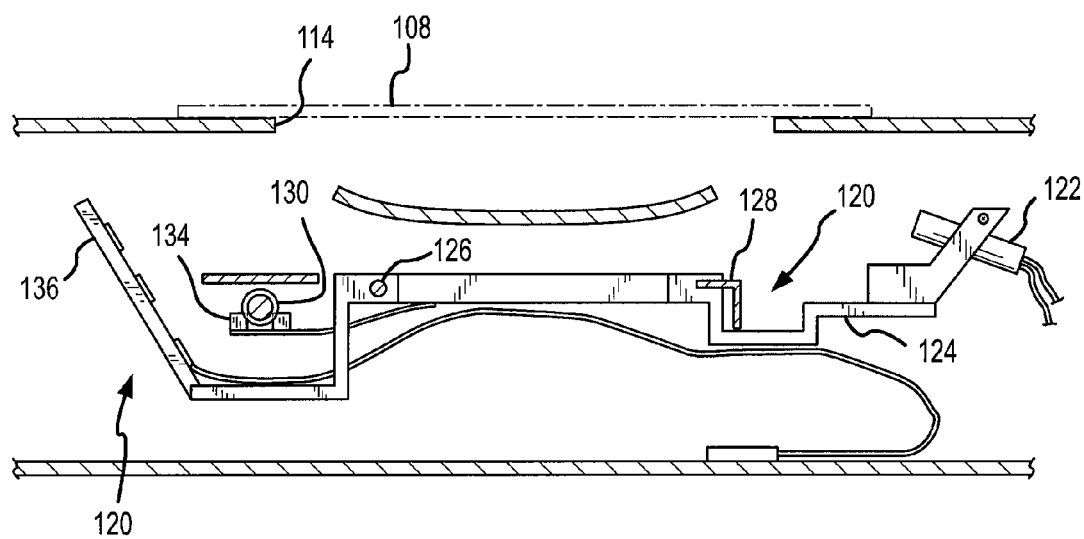
FIG. 4 is a section view taken along line 4-4 of FIG. 2.

FIGS. 2-4 illustrate one particular example of an optical certifier apparatus 100 conforming to aspects of the invention. The optical certifier includes a body structure 102 supporting a spring-loaded cover 104 that is positioned to cover an OSM stage 106 where the OSM 108 is positioned by a user. This implementation is configured to analyze surface defects of a DVD or CD type OSM. Accordingly, the stage includes a hub 110 that receives a central aperture of conventional DVD, CD or the like. The hub is attached to a motor 112 (see FIGS. 3A, 3B) that rotates the hub. The stage, hub, and related structure may be referred to as an OSM support and movement assembly. The OSM motor is adapted to rotate the hub supporting the OSM at a desired speed, such as 600 revolutions per minute (rpm). This motor may be equipped with a speed sensor to communicate when it is up to the desired speed, such as 600 rpm. The stage 106 further includes a window 114 positioned such that light from a light source 116 may be shown on the surface of the OSM 108 positioned on the stage, and reflected light captured by a detector 118.

Referring particularly to FIGS. 3A, 3B, and 4, the optical certifier 100 further includes a light generation and detection assembly and processing electronics. In the particular configuration of FIGS. 2A-4, the light generation and detection assembly 120 includes one or more lasers 122 or other light sources 116 arranged to be directed through the window 114 at the surface of an OSM supported on the stage. The light generation and detection assembly further includes one or more detectors 118 arranged to detect the light reflected from the surface of the OSM.

In the particular arrangement of FIGS. 2-4, both the laser and the detector are supported on a carrier 124. The carrier is moveably supported so that it may be moveably positioned relative to the OSM. In this particular configuration, the carrier is arranged to move radially with respect to the OSM 108 positioned on the hub 110. The carrier is supported on two rails 126, 128. Adjacent one rail 126, a worm gear 130 is coupled with a motor 132. A gear 134 is coupled with the carrier so that rotation of the worm gear moves the carrier.

On one side of the carrier 124, the laser 122 is coupled to the carrier. The laser is positioned to transmit light through the window 114 on the surface of the OSM. On the opposite side of the carrier, in this particular implementation, adjacent the worm gear 130, a printed circuit board 136 supports at least one detector. The PCB positions the detector(s) 118 to be positioned in the path of reflected light from the OSM. Arranged as shown in FIGS. 2-4, and discussed further below, rotation of the worm gear causes the laser and the detector to be scanned across the surface of the OSM. In FIG. 3B particularly, the light generation and detection assembly 120 is shown in phantom in an outer orientation, and also shown at a second position closer to the hub. This movement allows the laser to scan the OSM surface from its outer edge radially inward toward the inner aperture (hub).

In an alternative implementation, the laser/detector assembly is mounted on a pivoting bearing and configured to scan the OSM in an arc. In yet another alternative, the laser and detectors are mounted on separate assemblies that are moved substantially contemporaneously. Further, a light source that is adequately focused or adequately collimated or both is used to illuminate the surface of the OSD instead of a laser.

Aspects of the processing electronics are described in greater detail below with respect to FIG. 7. Output from the processing electronics is transmitted to a display 138, such as an LCD, positioned at the front of the certifier.

Figure 5:
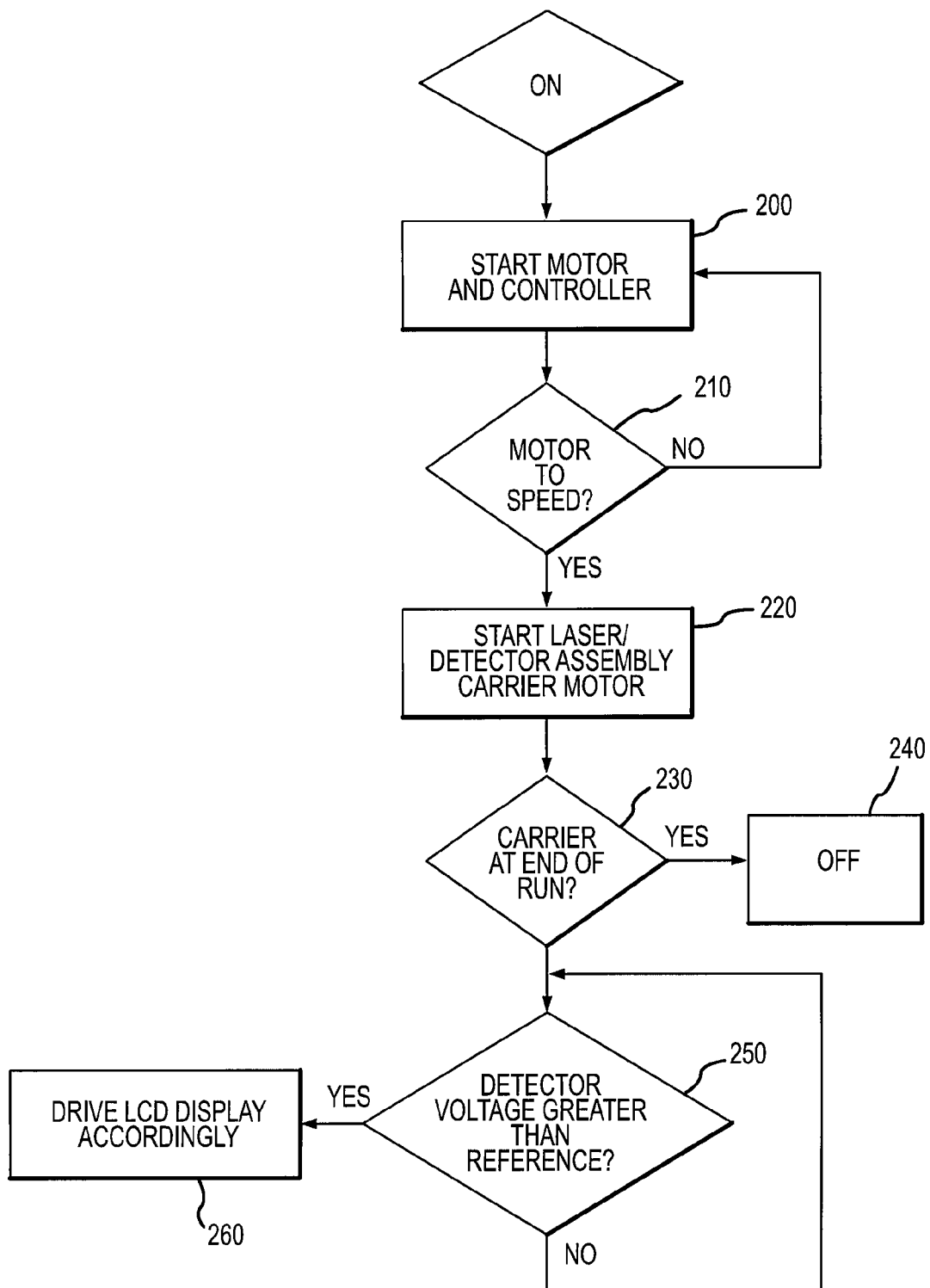
FIG. 5 is a flowchart illustrating one method of analyzing an optical storage media, confirming to aspects of the present invention.

FIG. 5 is a flowchart illustrating one particular method of analyzing an OSM surface to determine whether defects are present and whether the defects will affect readback or writing of data. To begin, an OSM is placed in the certifier on the hub and the motor is started to cause the OSM to rotate (operation 200). In one particular arrangement, the certifier 100 includes the lid 104 to at least partially cover the OSM and light source 116, detector 118, and other components during testing. The lid shields the detector assembly from ambient light to improve the signal to noise ratio. It also functions as part of an interlock system to protect the user's eyes from the laser. Alternatively, the OSM support and movement assembly, may be supported on a moveable tray that retracts the OSM support and movement assembly within an enclosed area and positions the assembly relative to the laser assembly. In either configuration, when the lid is closed or the tray retracted, a switch operatively coupled with the lid or tray, transmits a signal to an OSM motor controller which controls the spindle motor 112 causing it to start and rotate to the OSM at a set or variable speed. Alternatively, it is also possible to include a manually activated switch to cause the motor to activate and run at some speed. The certifier includes a power switch 140 which provides power to the device when switched on. It is also possible to include computer control or some other arrangement to cause the motor to activate.

Next, the motor speed is maintained to determine when the proper speed is reached (operation 210). In one embodiment, the spindle motor spin acceleration is monitored and used to determine the size of the disc under test, including whether there is no disc in place. For example, the motor will accelerate faster with no disc in place than with an approximately 8 cm game disc, such as a GameCube™ disc, under test which will in turn accelerate faster than an approximately 12 cm disc, such as a DVD. This information can be used to customize the type of test performed on the disc, including the thresholds used for damage detection, the equations used for damage score determination, or the amount of area scanned, among others.

When the desired speed is reached, the carrier motor 132 is activated to move the light source and detector assembly 120 so that the one or more light sources successively illuminates a spot or spots at various locations on the spinning OSM (operation 220). The light source/detector carrier 124 is moved so that, as the disc spins, the surface of the optical storage medium is in turn illuminated until the entire surface or a portion thereof has been sampled by the light source. In another embodiment, the carrier motor 132 is synchronized with the spindle motor 112, for example, by use of a once-around sync generated by the OSM motor, so that the carrier motor advances at a rate, which could be continuous or step-wise, determined by the spindle motor spin speed. In this case, the carrier motor can be activated while the spindle motor is accelerating, decelerating or at a variable speed and still successively illuminate the entire surface, or the desired portion of the surface, of the OSM. In one embodiment, for the minimum possible test time, the motor is continuously accelerated and then continuously decelerated to a stop such that the scan of the entire surface, or desired portion thereof, is completed just as the spindle motor comes to a stop. In the method of FIG. 5, the carrier moves until it has scanned the entire OSM surface, which is detected by reaching a radial endpoint near the hub. In any event, the certifier is configured to scan the surface and determine when the scan is complete (operation 230).

The reflection off the surface, depending on the presence or absence of defects, is directed toward or away from the detector, which in one particular implementation may be a photodiode. The surface of the OSD could be scanned in its entirety or partially. It can also be scanned once or multiple times before outputting the results, if desired. After the scan is completed, the motor turns off and brings the spinning OSM to a halt (operation 240).

As will be discussed in greater detail below with respect to FIGS. 6 and 7, the detector and processing electronics are configured to detect the reflected light, generate and output voltage, and compare the output voltage to a threshold voltage in one particular arrangement (operation 250). The threshold voltage is set to the output voltage associated with a certain level of surface defects that will affect proper OSM readback. The threshold voltage may be OSM type specific, OSD type specific, and related to other factors. Exceeding or not exceeding the threshold causes the appropriate LCD display, such as "pass" and "fail," respectively, or the like (operation 260).

Figure 6:
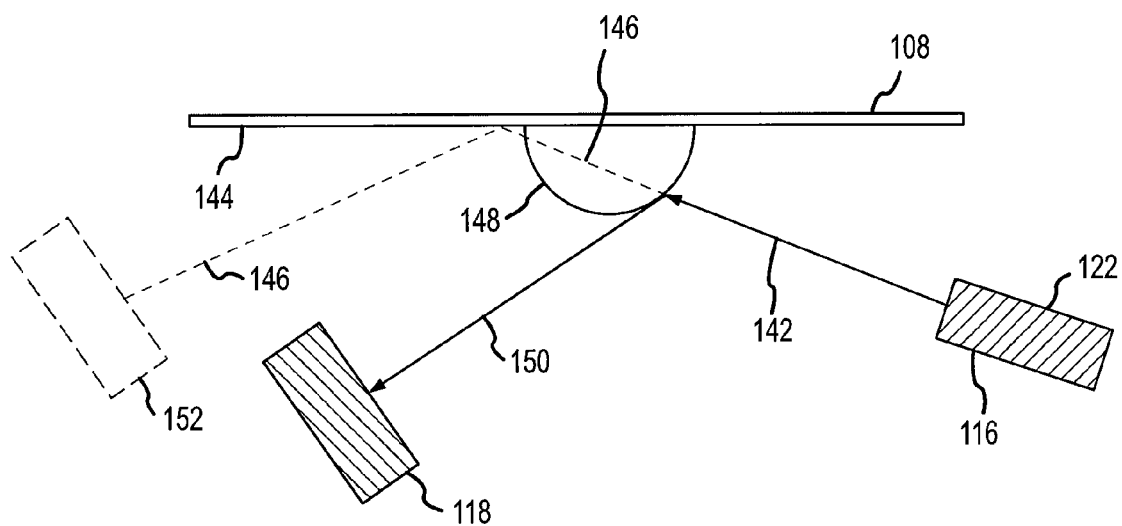
FIG. 6 is a diagram illustrating a laser incident on an optical storage media, a reflection of the laser off a defect on the optical storage media, and the collection of some portion of the reflected laser off the defect by a detector.

Referring now to FIG. 6, as well as other figures, the surface analysis technique is described in greater detail. The reflection of light 142 from a source 116 off a smooth unblemished surface 144 (no defect present in the illuminated area) of an OSM 108 is along a path 146 referred to as the principal axis (dashed line). In one particular arrangement, the detector assembly is arranged such that the light along the principal axis does not intercept a detector 118, so there is no signal to the electronics when the light is incident on an unblemished surface. When a defect 148, such as a scratch, is in the beam spot along the principal axis from the light source, the light is scattered from the surface and the path 150 of the reflected beam deviates from the principal axis. In one arrangement, the detector or detectors are arranged such that the scattered reflection from a defect will generally intercept a light-sensitive detector, thereby producing a signal that is detected by associated electronic circuitry, discussed in further detail below with respect to FIG. 7. It is possible for some defects to scatter light in a direction such that it is not intercepted by a detector. In this case, the defect would not be detected. This likelihood can be reduced by utilizing more detectors arranged around the principal axis, or by using a ring or partial ring of detectors, or a single detector of sufficient size (with the area that intercepts light along the principal axis masked out) that light that deviates from the principal axis intercepts the detector, or by using a photodiode with many light-sensitive pixels or a charge-coupled device that detects light on its many photosites or pixels, or by other methods.

The example illustrated in FIG. 6 employs a single laser 122 and associated optical detector 118, arranged to direct a laser to the surface 144 of the OSM 108 and collect the reflected light, or some portion thereof. Since defects can scatter incident light in various directions depending on their morphology, increased likelihood of detecting defects can be achieved by adding one or more lasers that intersect the OSM surface at a different incident direction or angle or both to the first laser or splitting the output of one or more light sources and directing the outputs to intersect the OSM surface at the same or a different incident direction or angle or both. Increased likelihood of defect detection can be achieved by adding one or more light-sensitive detectors at the same or different reflected direction or angle or both to the first light sensitive detector.

In the particular certifier illustrated in FIGS. 2-4, two detectors (118A, 118B) are arranged in a plane perpendicular to the direction of the principal axis 146 but at right angles to each other. Such an arrangement provides adequate sensitivity for certain purposes to detect defects oriented in random directions, including purely radial or purely circumferential.

Figure 7:
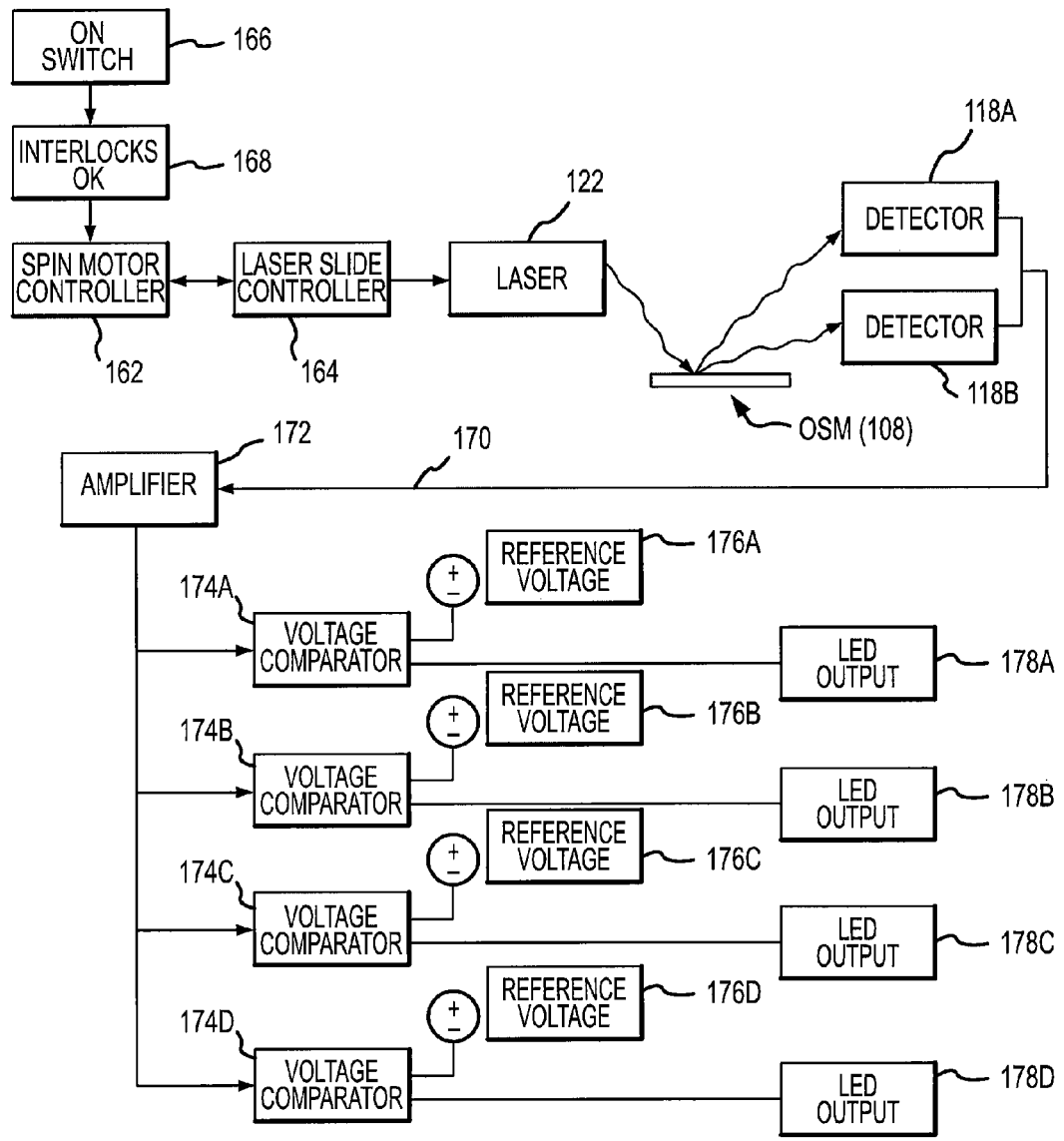
FIG. 7 is a block diagram illustrating the electronics of the analyzer shown in FIG. 1, conforming to aspects of the present invention.

FIG. 7 illustrates an electrical diagram for a certifier employing two detectors, which may or may not be arranged in a plane perpendicular to the direction of the principal axis but at right angles to each other. With the removal of one detector, the electrical schematic is substantially similar to that of a certifier employing one detector.

Referring again to FIG. 6, it is also possible to arrange a detector 152 (shown in phantom) along the principal axis and calibrate the system such that the light source, reflected off an unblemished, defect free surface, and impinging on the detector produces a known output signal. When a defect, such as a scratch, is in the area sampled by the illuminated area, the light is scattered from the surface and the path of the reflected beam deviates from the principal axis 146. This will lead to a reduction in the amount of light illuminating the detector 152 and a corresponding reduction in the output signal from the detector. These deviations from the known output may then be used to determine the presence of a defect. It is possible to arrange a certifier with an on axis detector 152, one or more off axis detectors 118, and combinations thereof.

The detector may take on various forms. A charge-coupled light sensitive device ("CCD") of sufficient size with multiple photosites or pixels can have the light impinge on certain photosites that are placed to intercept light along the principal axis. When the light is scattered by a defect in the surface, the photosites that intercept light along the principal axis will see a reduction in the amount of illumination and the photosites that are along the scattered path will see an increase in illumination as the light scatters off the defect. Such a detector integrates both on axis and off axis advantages.

Similarly, instead of a CCD with multiple photosites, multiple photodiodes, with one or more placed on-axis and one or more placed off the principal axis, could be used. If some or all of the scattered light is scattered such that it does not intercept the pixels that are not on the principal axis, then the off-axis detectors would not produce a signal, but the on-axis photodiode or diodes would see a reduction in the amount of light illuminating them and, correspondingly, produce a lower output signal.

In some embodiments, the reduction in the light illuminating the on-axis detector assembly due to a defect may be too small a fractional change in the overall illumination and the on-axis detector signal change will be small. In this case, the off-axis detectors can still show a signal that can be acceptably reliably detected. Therefore, off-axis detector, on-axis detector, or some combination thereof may be usefully employed in embodiments conforming to aspects of the present invention.

Figure 8:
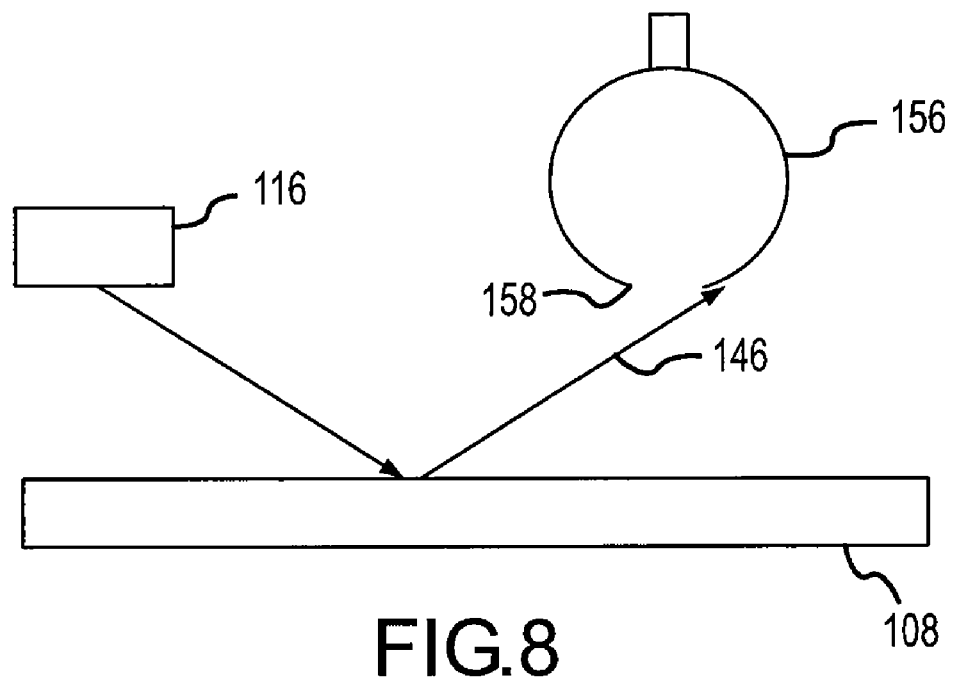
FIG. 8 is a diagram illustrating a laser reflected from an unblemished surface of an optical storage media and incident on an optical sphere detector in accordance with aspects of the present invention.
Figure 9:
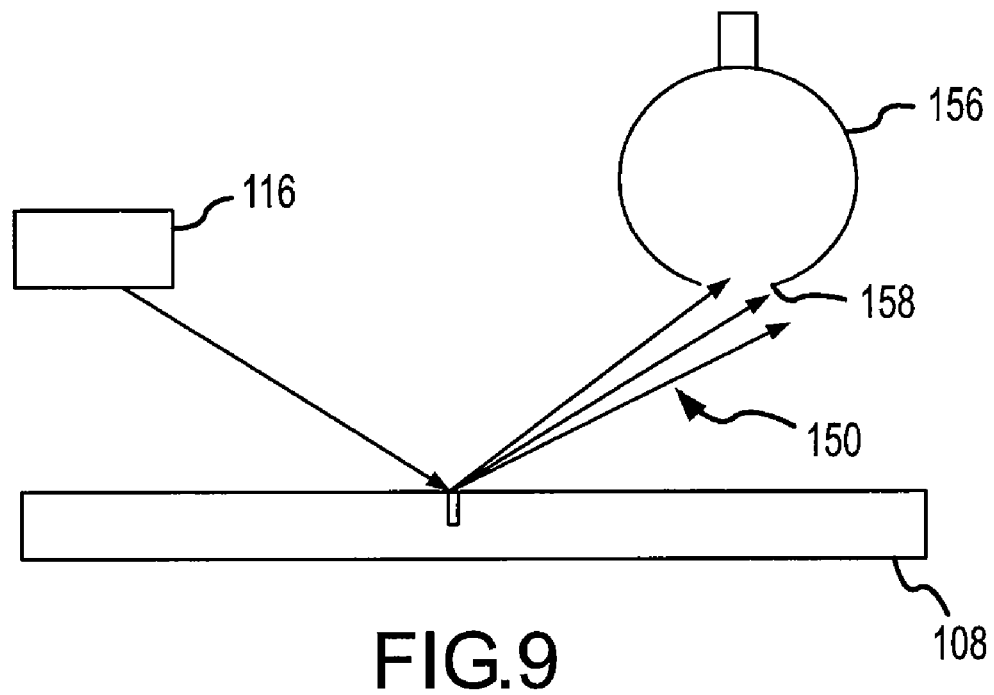
FIG. 9 is a diagram illustrating a laser reflected from a blemished surface of an optical storage media and incident on the optical sphere detector of FIG. 8, in accordance with aspects of the present invention.
Figure 10:
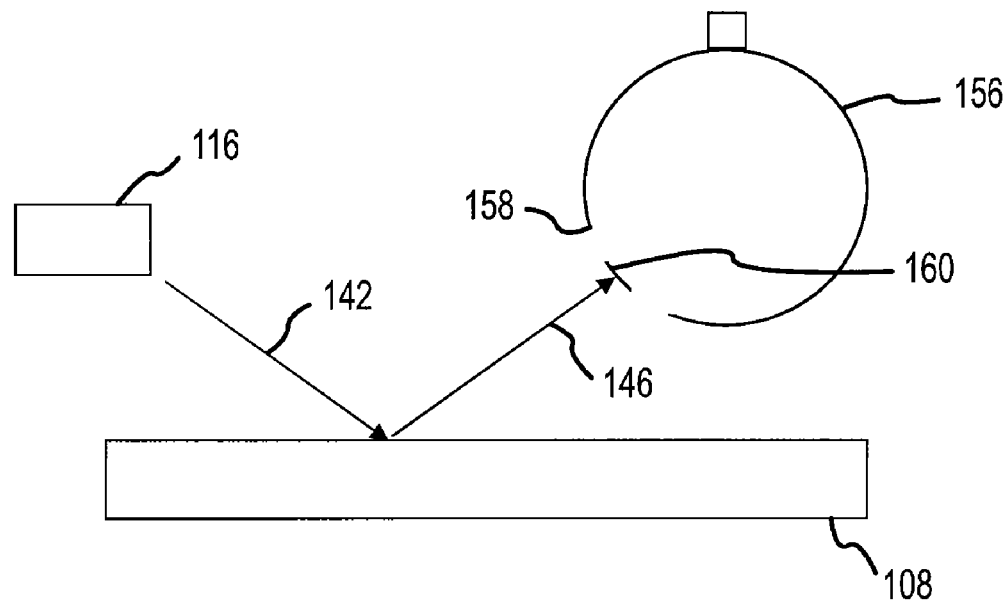
FIG. 10 is a diagram illustrating a laser reflected from an unblemished surface of an optical storage media and incident on an optical sphere detector with a masked aperture, in accordance with aspects of the present invention.
Figure 11:
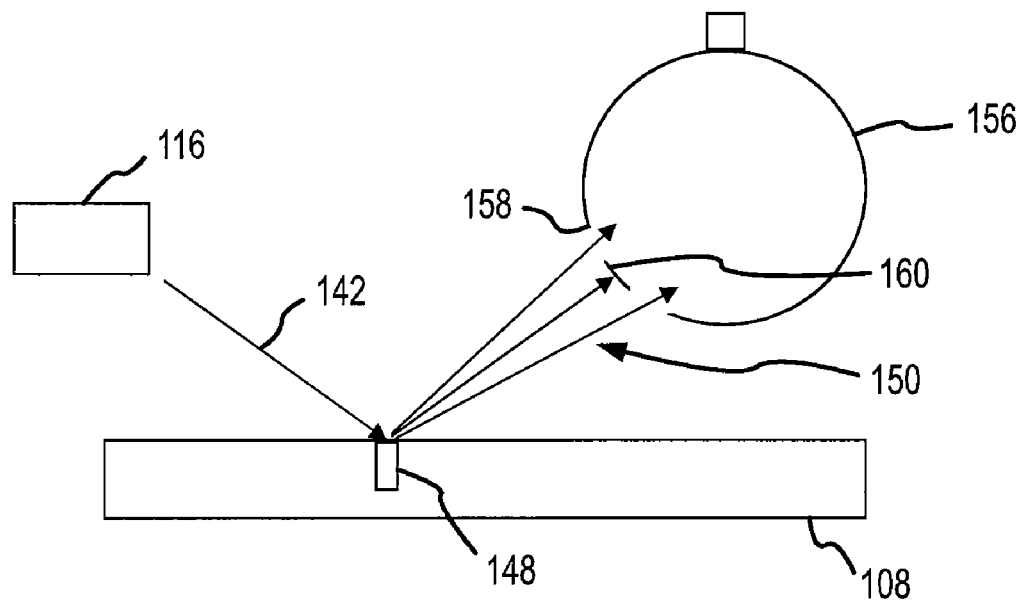
FIG. 11 is a diagram illustrating a laser reflected from a blemished surface of an optical storage media and incident on the optical sphere detector as shown in FIG. 10, in accordance with aspects of the present invention.
Figure 12:
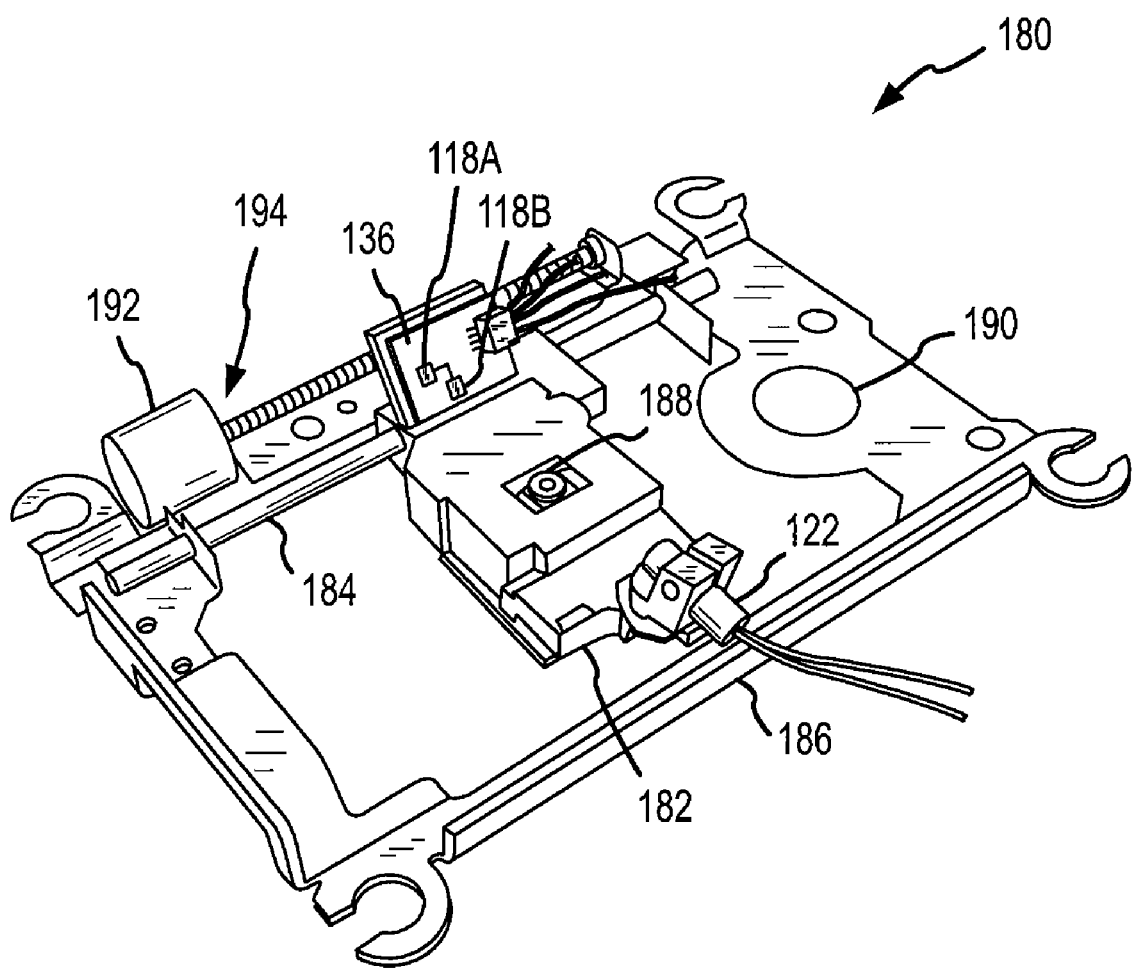
FIG. 12 is an isometric view of certifier components integrated with a DVD read back device, in accordance with aspects of the present invention.

As shown diagrammatically in FIGS. 8-9, it is also possible to use an integrating optical sphere 156 to gather the scattered light 150 from the laser 116. In one arrangement shown in FIG. 8, the sphere includes an aperture 158 that is arranged adjacent, but not along, the principal axis 148. Accordingly, as shown in FIG. 9, when the light encounters a defect on the OSM 108, some portion of the light 150 scattered from the defect will be directed into the aperture. Internally, the sphere reflects the light and provides an output commensurate with the detected light. Similar optical methods for gathering light can be employed in embodiments conforming to aspects of the present invention. For example, a single detector could be used but in conjunction with a reflective surfaces or surfaces, or refractive surface or surfaces, or both to collect the light scattered by the damage and direct it to the single detector. As shown in FIGS. 10-11, the integrating optical sphere may include a mask 160 on the principal axis such that light along the principal axis does not enter the sphere but light 150 that has been scattered from a defect does enter the sphere to be detected. In this example, the aperture is open on all sides around the mask, and hence around the principal axis. In the first sphere example, the entire aperture is located off-axis, thus light scattered to the opposite side of the principal axis may not be detected.

Referring again now to FIG. 7 and others, the OSM motor 112 and laser/detector assembly motors 132 are controlled by respective controllers (162, 164). The spin motor is responsive to the lid switch, tray switch, or manual switch, and may also require a verification that the lid or tray is in a lock position, which may also be provided from a signal from a switch, separate or the same as the lid or tray switch and an interlock signal (166, 168). Laser 122 illumination may be triggered from the OSM motor controller, the laser/detector assembly motor controller, or by other means. The laser or other light source impinges on the OSM 168 surface and light reflected therefrom intercepts one or more detectors. The detectors (118A, 118B) generate output voltages (170) as a function of the amount of incident light which may be just the noise level voltage if there are no defects causing light to be incident on the detectors. The output voltage is transmitted to one or more amplifiers and/or filters 172. The amplifier or amplifiers are coupled with one or more associated comparator circuits (174A-174D). Each comparator circuit is provided with a reference voltage (176A-176D). Further, each comparator circuit is coupled with one or more light emitting diodes ("LEDs") or other output devices.

In the particular arrangement of FIG. 7, the output from the detectors is coupled with four comparator circuits. Each comparator circuit has a unique threshold voltage. Further, each comparator circuit normally drives a green LED, and upon meeting the threshold drives a red LED (LED outputs 178A-178D). Alternatively, each comparator output is arranged to drive a respective LCD display, as "Pass," Some Damage But Will Play", "Fail Level 1," "Fail Level 2," and "Fail Level 3."

When the laser 122 is incident upon a defect, the light is generally briefly intercepted by the light-sensitive detector(s) 118A, 118B which produces the output voltage 170. This detector voltage signal is summed and amplified by the amplifier 172 and, using the comparator circuitry 174, is compared to the reference voltage(s) 176. In one particular implementation, if the reference voltage is exceeded, then a red LED is illuminated and a green LED is turned off to signal to the user that this reference voltage has been exceeded. It has been found that there is an approximate and sufficient correspondence between the amplitude of the detector signal and the likelihood that the defect that scattered the light that created the corresponding signal will prevent a DVD from playing accurately.

One or more comparator circuits, using the same or different reference voltages, coupled with a green and red LED pair, can be used to provide an approximate scale of damage.

If the red LEDs corresponding to the higher reference voltages are triggered, then it has been found that it is likely that a more extensive defect is present, which in turn indicates that the defect is more likely to interfere with proper read back of the OSM and correction of the defect is more difficult.

The reference voltages to the comparator circuits can be fixed or can be adjusted by the user. In one embodiment, a single comparator circuit with an adjustable reference voltage controlled by a potentiometer or similar device accessible to the user can generate the same approximate scale of damage by testing the OSM multiple times with different reference voltages. In another embodiment, the reference voltage is provided by a digital to analog converter and set via a software update from an attached computer or other device. In another embodiment, the digital reference level is compared to the computed damage level inside the microcontroller or DSP controller.

In another embodiment, the resulting damage level is displayed on the LCD screen 138 based on the output from the comparators. In yet another embodiment, the damage level is outputted to a separate device, such as a personal computer or point-of-sale terminal, using a interface such as USB 2.0 and displayed on the separate device.

In one particular certifier implementation, a DigiKey model no. 38-1000-ND laser and Hammamatsu model no. S1787-08 Photodiode detectors are employed. The first comparator 174A has a 1 V reference voltage, the second comparator 174B has a 2 V reference voltage, the third comparator 174C has a 3 V reference voltage, and the fourth comparator 174D has a 4 V reference volt. Based on a correlation to several DVD players currently available in the market used as references, such as Philips DVP642, Samsung DVD-L70, Hitachi DVP755U, or Sony DVP-NS575P/S, it has been determined that an amplified photodiode output between 1 and 2 volts, which would cause illumination of the red LED 178A by the first comparator circuit, but would not illuminate the second through fourth LEDs 178B-178D indicates that the DVD being analyzed would play on these players, but some defects are nonetheless present. A voltage of 2 volts or greater, illuminating the second 178B through fourth 178D red LEDs, depending on the voltage, indicates that the subject DVD has defects sufficient to inhibit or prevent play of the DVD on these reference players. Increasing output voltage generally corresponds with a greater degree of defect. The particular threshold voltage or voltage for any particular implementation can depend on various factors, including the type and power of laser employed, the output voltage of the detector employed, the type and amplification range of the comparator arrangement employed, if any. Further, the threshold values may be optimized in any particular arrangement depending on the type of OSM, the type of protective coating, the type of expected use, customer issues, as well as other factors.

In other embodiments, the amplified signal from the detector can also be integrated to provide an approximate measurement of the total amount of damage present on the disc. In another embodiment, the comparator circuitry 174A can also be monitored by an optional counter so that the number of defects exceeding the given threshold or thresholds can be measured. In another embodiment, the output signal can be analyzed by a peak sample-and-hold circuit that outputs the peak signal detected until it is reset. This peak signal can be converted using an analog-to-digital converter and output as a voltage, it can be used to drive an analog dial or needle indicator, or other methods.

In another embodiment, the output from the detector arrangement, or a portion thereof, can be digitally sampled, analyzed, and output in a number of ways that will be obvious to those skilled in the art. In one particular certifier implementation, two detectors are placed off-axis and orthogonal to each other. In one particular implementation, the detectors are Osram™ model BPW34S or Fairchild™ QSB34CGR detectors. The amplified signal is routed to a digital signal processing ("DSP") chip, such as Texas Instruments 32-bit Fixed Point DSP TMS320F2808, which is operating at an analog input sample rate of 20 kHz. The signals are fed separately to two analog inputs on the DSP and a "damage level" computed as follows:

$$\text{Damage level} = \{A^*(V1) + B^*(V2)\}/M$$

where V1 and V2 are the digitized voltage from the detectors and A, B, and M are adjustable parameters dependent on the desired weighting of the voltage from each detector. In another embodiment, the damage level is computed as follows:

$$\text{Damage level} = \text{square root } \{A^*(V1)^2 + B^*(V2)^2\}/M$$

In either event, the damage level is displayed for the user. The weighting values can be determined by the relative importance of the defects that scatter light to each detector or based on a calibration of detector sensitivities, or both, or for other reasons. For example, each detector does not necessarily produce the exact same output signal as another detector for the same given illumination. By weighting the digitized voltage of the detectors accordingly in the damage level calculation, this effect can be reduced to an acceptable level for each application.

In addition, for various OSM, the orientation of a defect can be related to the likelihood that the data will not be read. For example, in a typical DVD player, a defect that proceeds circumferentially around the disc, thereby rendering unreadable a long successive or interleaved section of data, is more likely to result in uncorrectable errors than a radial scratch that periodically obscures a shorter portion of data. In this case, it is desirable for the damage level to be higher for a defect that is circumferential or substantially circumferential than a similar defect that is radial or substantially radial. This damage score can be normalized and rounded or truncated for convenient display.

In one embodiment, the highest damage level measured is outputted to the user via the LCD 138 or communicated to an external device such as a PC or point-of-sale terminal. In another embodiment, the number of events where the damage level exceeded a certain threshold or thresholds can be outputted. In another embodiment, the signal can be integrated over the entire signal, or a portion thereof, and the resulting value used as a measure of overall damage. The damage level as a function of location on the disc can be recorded and displayed in the form of a map of the OSM showing damaged or undamaged areas. The damage level can be related to the amount of repair required to reduce the damage level to a defined threshold and the amount of repair required can be displayed, It is also possible to continually output the damage level for analysis or display. In yet another embodiment, the signal is not analyzed by the DSP but stored and transmitted to another device, such as a computer or disc polishing device, for analysis.

In cases where a plurality of detectors is used, the damage level can be computed as:

$$\text{Damage level} = \text{square root } \{A^*(V1)^2 + B^*(V2)^2 + C^*(V3)^2 + D^*(V4)^2 + \ldots\}/M$$

$$\text{Damage level} = \{A^*(V1) + B^*(V2) + C^*(V3) + D^*(V4) + \ldots\}/M$$

In another embodiment with an on-axis detector and two off-axis detectors, the signal from the off-axis detectors can be subtracted from the on-axis detector. When light is scattered by damage, the voltage at the on-axis detector is reduced and the voltage at the off-axis detector is increased. By mathematically combining these two changes—the reduction in voltage at the on-axis detector and the increased voltage at the off-axis detector, the signal to noise ratio at the analyzing electronics can be increased.

Other equations for computing a damage level from the digitized sample from one or more detectors can be used in implementations conforming to aspects of the invention. The on-axis detector signal may arranged to vary with the reflectivity of the disc. A surface that is more reflective will result in a higher average voltage produced by the on-axis detector. This varying signal, possibly in conjunction with the disc size information determined as discussed above, can be used to determine which type of disc (for example, Blu-Ray, HD-DVD, DVD-ROM, game disc) is being measured and customize the type of test performed on the disc, including the parameters used in the damage score, the thresholds used for damage detection or for pass/fail determination, the equations used for computing a damage score, or the amount of area scanned, among others. In some discs designed to be recorded by users, the recorded data changes the reflectivity of the underlying surface. This change in reflectivity can be used to identify areas with data and areas without data. A defect in an area without data is not detrimental to readback as is a defect in the area without data. On the other hand, a defect in an area currently without data is detrimental to writing additional data to the disc. For example, some game discs, such as certain Sony Playstation™ 2 discs, have a black surface instead of a shiny aluminized surface to store the data. Since a dark surface will absorb more light than a shiny one, the amount of light that is reflected is reduced. Correspondingly, the amount of light that is scattered from a defect on a black game disc is also reduced compared to the light that would be scattered from a similar defect on a standard DVD disc. The threshold for the damage level needs to be changed to account for this change. When a dark coated disc is measured, the signal from an on-axis detector will be reduced compared to the signal produced by a standard shiny DVD. This reduction in signal can be used to identify the type of disc in the player. The measurement process, the damage level calculation, the damage level thresholds can all be customized with this information.

Embodiments may be provided in a standalone device or "optical certifier" that can rapidly analyze an OSM surface. Such a standalone device might be suitable for a company that rented DVDs or other OSM or otherwise allows access to consumers or other third parties, to ensure that their inventory of DVDs would play or allow data access properly when the consumer uses them. An optical certifier can additionally be integrated into the company's computerized inventory or point-of-sale system to record the damage history of the OSM or the history of the consumer in damaging OSMs. Further, the thresholds could be set for each particular customer as the company received feedback from them and determined that their OSD was particularly sensitive or robust in regard to reading or writing through defects. This standalone device would incorporate a motor to spin the disc, a method for scanning the laser or lasers along the radius of the disc as it spins, and circuitry to make the measurements, as discussed above.

Methods and configurations set forth herein can also be integrated into an existing OSD, such as a DVD player/recorder or CD player/recorded, to scan the disc before starting the playback or write sequence to determine, in advance, if the disc can be read or written all the way through, or whether some defects may affect data access or storage. This might be advantageous, for example, to a company making DVD players.

One example of an integrated player/certifier is illustrated in FIG. 10. This integrated device could include some or all the features of the stand-alone device or, more advantageously, use certain features already existing in the OSM read back device, such as, but not limited to, the OSM motor, the OSM support, the laser slide assembly, the laser, the optics, such as the lens, the detector, and various features of the electronics. In one exemplary embodiment for an OSD such as a DVD player, a separate laser and detector assembly are added to the existing laser slide assembly as shown in FIG. 10.

More particularly, the alternative certifier 180 implementation includes the laser 122 and detectors 118A and 118B (and related PCB 136) mounted on a conventional DVD player laser assembly 182. The laser assembly is mounted on opposed rails 184, 186. The conventional DVD read write laser 188 is supported in about the middle of the laser assembly, with the laser 122 and detectors 118 at either end. Only a portion of the assembly is shown, for ease of reference the aperture 190 is axial arranged with a conventional DVD player motor and hub. Accordingly, the rails are positioned to move the laser assembly radially with respect to a DVD mounted in the device. A motor 192 operatively coupled with a worm gear arrangement 194 moves the laser assembly 182, and hence the laser 122 and detectors 118A and 188b, back and forth along the rails.

It is also possible to use the conventional laser 188 is a dual role of certifier laser and read/write laser. In such an arrangement, either the laser orientation is altered to so that some light reflected from a defect is scattered to the detectors 118, or the detectors are rearranged to detect light reflected from a defect with the illustrated positioning of the laser 188. Other possible laser or detector arrangements are also possible that provide for dual user of the read/write laser.

A comparator circuit such as that described in FIG. 7 is added to the existing electronics. In this embodiment, the OSM is spun up by the DVD player motor, the DVD laser slide 182 is moveably actuated across the disc, the separate laser 122 is energized and the output from the separate detector assembly 118 is monitored by the comparator circuit to signal the OSD whether the OSM can be accurately read or written. The threshold can be customized for the capabilities of this particular OSD rather than the stand-alone certifier case where the thresholds are generally, but not necessarily, set to accommodate the characteristics of a variety of OSDs. The thresholds for successful read back and successful writing can be either the same or different.

Methods and/or devices that can repair certain types of damage on OSM exist. Equipment used for repairing damaged discs generally uses different repair methods, including different time spent performing the repair method, depending on the nature of the damage. Often the different types of methods are codified into fixed programs that the user can select. In some cases, the different types of methods may have variable parameters, such as the time of each abrasive or polishing operation that the user can select. It is desirable to select the program that will repair the defect to a certain minimum level of playability, but not remove more material than is necessary to maximize the number of repairs that can be performed on a given disc before the protective material is entirely removed. In OSM-based businesses that utilize repair systems, the decision on which of the methods or parameters is suitable for a given defective disc is a recurring problem.

Typically, the decision is made by visual inspection. The several disadvantages in this approach are that different people may judge the required repair differently, that they may judge the required repair incorrectly, leading to an over-aggressive repair or an incomplete repair, and the recurring cost of training employees to make said distinctions. In one embodiment, the OCD be used to quantify the nature of damage and may then be configured to measure the disc and display the proper method or program via a display method such as LCD readout or display screen or, even more advantageously, can communicate directly with the repair equipment to set the proper program to achieve a certain level of repair. After the repair, the OCD can be used again to verify that the repair or cleaning was successful.

In another embodiment, the automated repair system that takes a stack of unsorted discs, the OCD module measures each disc and determines the appropriate repair program, then the repair module executes the given program, and then passes the OSM to the output. In one embodiment, the OCD determines which disc do not need repair and passes these discs directly to the output. In another embodiment, the quality of the repair can be checked by returning the repaired disc to the OCD to ensure that a minimum level of playability was achieved. In this way, a large number of discs can be efficiently and accurately repaired without operator intervention. This is also advantageous for unattended kiosk-based OSM businesses.

The method could be integrated into a system incorporating disc cleaning or repair methods to provide a mechanism that could determine if a cleaning or repair were necessary, then clean or repair the OSM, and then determine if the cleaning or repair were adequate.

In accordance with the various implementations set forth herein, further alternative implementations may be configured in accordance with aspects of the invention. For example, the light source beam can be reflected off a movable, including spinning, reflective surface or other optical device that allows the area of illumination spot to successively sample the entire surface, or desired portion of the surface, of the OSM as it rotates instead. In another example, in an player/certifier integrated device, the output from the detectors 118 can be directed to an existing player DSP chip, microcontroller, or Analog to Digital converter, or other conventional player electronics to make the measurements and/or calculation that indicate whether the disc can or can not play in that specific OSD.

In another example, the OSD laser is used to generate the light, but one or more stationary mounted detectors are used to detect scattered light from surface damage. Alternatively, one or more stationary lasers or other light source are directed upon the disc and the OSD detector is scanned relative to the disc. In any implementation, depending on the orientation of the light source (or sources), the orientation of the detector (or detectors), and whether the light source, detector, or both, are moveably mounted, the OSM may or may not be rotated. In various implementations, to enhance detection of scattered light, a reflective surface or surfaces or a refractive device or devices may be used to direct the scattered light upon the detector(s).

The OSM can also be moved linearly, without rotating, past the light source/detector assembly. The light source/detector assembly is mounted to allow it to move orthogonal to the direction of the OSM movement such that the entire surface, or some desired portion thereof, can be scanned. In another alternative, the light source beam can be reflected off a movable, including spinning, reflective surface, such as a mirror or other optical device that allows the area of illumination spot to successively sample the entire surface, or desired portion of the surface, of the OSM as it moves linearly past. The detector assembly can be mounted movably such that it intercepts the reflected light from the OSM. Alternatively, the reflected light from the OSM can be collected by reflective or refractive optical elements and focused on the detector assembly which can be movable or fixed in this case.

In another embodiment, the illumination from the light source can be in the shape of a line of light which extends from one edge to the other edge of the OSM, or some portion of that distance, such that the entire surface, or desired portion of the surface, of the OSM is illuminated and sampled as it moves linearly past. In the case where the line extends at least from edge to edge of the OSM or at least to cover the desired portion of the OSM, the light source may be fixed. In the case where the illumination line covers a portion of the distance form edge to edge, the illumination source can be movable such that the desired portion of the OSM surface is sampled. The length of the line can also be varied as the OSM moves linearly past in order to scan the portion of the OSM surface desired. To capture the reflected light, the detector element can be movable itself, or the reflected illumination can be directed by movable or fixed reflective or refractive elements, or a combination thereof to the detector assembly. The detector elements can also be in the form of a line, such as a line of photodiodes or a CCD device, that substantially correspond to the area illuminated by the light to allow the detector assembly to intercept the desired amount of the light.

In another embodiment, the illuminated area of the OSM surface can be in a spot that is movable to allow it to sample the desired portion of the OSM surface while the detector assembly is fixed but is of the shape and orientation such that it intercepts the reflected light as desired.

Aspects of the present invention are applicable in any context where a readback or recording mechanism transmits to and/or receives light, which may be visible light, from a storage medium, such as an OSM, to obtain data from or store data on the storage medium. The data is read by detecting the way light is transmitted or reflected. The medium containing the data is protected by a surface, possibly optically transparent, that can be damaged, modified, either temporarily or permanently, such that the damage, etc., modifies the way the light is transmitted or reflected independent of the data below.

Although various representative embodiments of this invention have been described above with a certain degree of particularity, those skilled in the art could make numerous alterations to the disclosed embodiments without departing from the spirit or scope of the inventive subject matter set forth in the specification and claims. All directional references (e.g., upper, lower, upward, downward, left, right, leftward, rightward, top, bottom, above, below, vertical, horizontal, clockwise, and counterclockwise) are only used for identification purposes to aid the reader's understanding of the embodiments of the present invention, and do not create limitations, particularly as to the position, orientation, or use of the invention unless specifically set forth in the claims. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other.

In some instances, components are described with reference to "sides" having a particular characteristic and/or being connected to another part. However, those skilled in the art will recognize that the present invention is not limited to components which terminate immediately beyond their points of connection with other parts. Thus, the term "side" should be interpreted broadly, in a manner that includes areas adjacent, rearward, forward of, or otherwise near the terminus of a particular element, link, component, member or the like. It is intended that all matter contained in the above description or shown in the accompanying drawings shall be interpreted as illustrative only and not limiting. Changes in detail or structure may be made without departing from the spirit of the invention as defined in the appended claims.

The invention claimed is:

1. A method for analyzing the surface of an optical storage medium comprising:
   directing at least one light signal on an outer surface of an optical storage medium, the optical storage medium including encoded data on a recording layer, the recording layer underlying the outer surface;
   detecting some portion of the at least one light signal reflected from the outer surface of the optical storage medium;
   determining defects in the outer surface as a function of detecting some portion of the at least one light signal reflected from the outer surface; and
   based on the defects in the outer surface, determining whether the encoded data may be accurately read from the recording layer.

2. The method of claim 1 further comprising providing relative movement between the optical storage medium and the at least one light signal.

3. The method of claim 2 wherein the operation of providing relative movement between the optical storage medium and the at least one light signal comprises rotating the optical storage medium.

4. The method of claim 2 wherein the operation of providing relative movement between the optical storage medium and the at least one light signal comprises moving a source of the at least one light signal relative to the optical storage medium.

5. The method of claim 2 wherein the operation of providing relative movement between the optical storage medium and the at least one light signal comprises moving the optical storage medium relative to the at least one light signal.

6. The method of claim 1 wherein the operation of directing at least one light signal on an outer surface of an optical storage medium comprises directing at least one light signal on a coating of the outer surface of the optical storage medium.

7. The method of claim 1 wherein the determining operation comprises determining a likelihood of accurately reading the data encoded on the optical storage medium as a function of the detection of the at least one reflected light signal.

8. The method of claim 7 wherein the operation of detecting further comprises providing an output signal that is a function of the detected portion of the at least one light signal.

9. The method of claim 8 wherein the operation of determining comprises comparing the output signal with a reference signal.

10. The method of claim 9 further comprising comparing the output signal with a first reference voltage, a second reference voltage, a third reference voltage and a fourth reference voltage, wherein each reference voltage is associated with defects of the optical storage medium that are associated with the likelihood of accurately reading the data encoded on the optical storage medium.

11. The method of claim 1 wherein the at least one light detector includes a first light detector and a second light detector, and the operation of determining comprises computing a damage level according to the formulation:

damage level=square root $\{A*(V1)^2+B*(V2)^2\}/M$ where V1=digitized voltage from a first light detector, V2=digitized voltage from the second light detector, and A, B, and M are adjustable parameters dependent on the desired weighting of each detector.

12. The method of claim 1 wherein the at least one light signal comprises a laser light signal.

13. An apparatus for analyzing an optical storage medium comprising:
   a platform configured to support the optical storage medium, the optical storage medium defining at least one side having a data layer;
   at least one light positioned to illuminate the at least one side having a data layer along a principal axis;
   at least one off-axis light detector not positioned along a principal reflected axis, the principal reflected axis being the path taken by light reflected from a substantially unblemished surface of the optical storage medium and incident on the unblemished surface along the principal axis, the at least one off-axis light detector positioned to receive light reflected from the optical storage medium and provide an output signal as function of the received reflected light; and
   at least one circuit element configured to receive the output signal from the light detector and to provide an output indicative of the integrity of the at least one side having a data layer.

14. The apparatus of claim 13 further comprising: at least one on-axis light detector positioned along the principal reflected axis.

15. The apparatus of claim 13 wherein the at least one off-axis light detector is a charge coupled device.

16. The apparatus of claim 13 wherein the at least one off-axis light detector is a photodiode.

17. The apparatus of claim 13 wherein the at least one circuit element comprises at least one comparator configured to compare the output signal from the at least one light detector to a reference voltage and provide a comparator output indicative of the integrity of the at least one side having a data layer.

18. The apparatus of claim 13 wherein the at least on circuit element comprises a digital signal processor.

19. The apparatus of claim 13 wherein the at least one light detector comprises a first light detector positioned off-axis from the principal reflected axis and a second light detector positioned off-axis and orthogonal to the first light detector.

20. The apparatus of claim 13 wherein the at least one circuit element comprises a digital signal processor configured to compute a damage level according to the formulation:

damage level=square root $\{A*(V1)^2+B*(V2)^2\}/M$ where V1=digitized voltage from the first light detector, V2=digitized voltage from the second light detector, and A, B, and M are adjustable parameters dependent on the desired weighting of each detector.

21. The apparatus of claim 13 wherein the platform includes a motor operably coupled with a hub configured to support the optical storage medium, the motor configured to rotate the hub and supported optical storage medium.

22. The apparatus of claim 13 further comprising a moveably mounted carrier supporting the at least one light and the at least one detector.

23. The apparatus of claim 22 wherein the carrier includes a gear, and further comprising a worm gear operably coupled with the gear.

24. The apparatus of claim 13 wherein the at least one light is a laser.

25. The apparatus of claim 13 wherein the at least one circuit element is configured to receive a signal from the at least one light detector and to provide an output indicative of the integrity of a coating on the at least one side having a data layer.

26. The apparatus of claim 13 wherein the at least one light is arranged to move relative to the at least one light detector in order to scan some portion of the optical storage medium.

27. The apparatus of claim 13 wherein the at least one light detector is arranged to move relative to the at least one light in order to scan some portion of the optical storage medium.

28. The apparatus of claim 13 wherein the platform is configured to support the optical storage medium to provide relative movement with respect to at least one of the at least one light and the at least one light detector.

29. The method of claim 1 further comprising the operation of computing a damage level.

30. The apparatus of claim 13 wherein the at least one circuit element comprises a processor configured to compute a damage level.

31. An apparatus for analyzing an optical storage medium comprising:
    means for supporting an optical storage medium;
    means for directing a light signal on an outer surface of the optical storage medium, the optical storage medium including encoded data on a recording layer, the recording layer underlying the outer surface;
    means for detecting some portion of the light signal reflected from the optical storage medium and providing at least one output signal; and
    means for assessing the output signal to determine the integrity of the outer surface of the optical storage medium;
    means for assessing whether the encoded data may be accurately read from the recording layer based on the integrity of the outer surface of the optical storage medium.

* * * * *